United States Patent [19]

Kim et al.

[11] Patent Number: 5,498,690

[45] Date of Patent: Mar. 12, 1996

[54] USE OF POLYCONDENSATION PRODUCTS, AND NOVEL POLYCONDENSATION PRODUCTS

[75] Inventors: Son N. Kim, Hemsbach; Axel Sanner, Frankenthal; Karin Sperling-Vietmeier, Neustadt, all of Germany

[73] Assignee: BASF Aktiengesellschaft, Ludwigshafen, Germany

[21] Appl. No.: 373,275

[22] PCT Filed: Jul. 17, 1993

[86] PCT No.: PCT/EP83/01887

§ 371 Date: Jan. 27, 1995

§ 102(e) Date: Jan. 27, 1995

[87] PCT Pub. No.: WO94/02110

PCT Pub. Date: Feb. 3, 1994

[30] Foreign Application Priority Data

Jul. 27, 1992 [DE] Germany .......................... 42 24 761.6

[51] Int. Cl.⁶ .............................. C08G 63/12; A61K 7/06
[52] U.S. Cl. .......................... 528/296; 424/47; 424/70.1; 424/70.11; 424/70.16; 528/176; 528/271; 528/282; 528/290; 528/291; 528/292; 528/293

[58] Field of Search ..................... 424/47, 70, 71, 424/72; 528/176, 271, 290, 291, 292, 293, 296, 282

[56] References Cited

U.S. PATENT DOCUMENTS

| 3,523,998 | 8/1970 | Feinstone et al. . | |
|---|---|---|---|
| 3,734,874 | 5/1973 | Kibler et al. . | |
| 4,150,216 | 4/1979 | Quack et al. ............................ | 528/290 |
| 4,300,580 | 11/1981 | O'Neill et al. . | |
| 4,867,966 | 9/1989 | Grollier et al. ............................ | 424/71 |
| 5,009,880 | 4/1991 | Grollier et al. ............................ | 424/47 |

FOREIGN PATENT DOCUMENTS

| 2637167 | 5/1977 | Germany . |
| WO89/07118 | 8/1989 | WIPO . |

*Primary Examiner*—Shelley A. Dodson
*Attorney, Agent, or Firm*—Oblon, Spivak, McClelland, Maier, & Neustadt

[57] ABSTRACT

Carboxyl-containing polycondensation products having glass transition temperatures $T_G \geq 20°$ C. obtained from anhydrides of tricarboxylic or tetracarboxylic acids and diols, diamines or amino alcohols are used for cosmetic purposes, in particular as hair treatment compositions.

8 Claims, No Drawings

USE OF POLYCONDENSATION PRODUCTS, AND NOVEL POLYCONDENSATION PRODUCTS

RELATED APPLICATIONS

This application was filed as PCT International application Ser. No. PCT/EP 93/01887 on Jul. 17, 1993.

In cosmetics, hair treatment compositions which, for example, are in the form of styling lotion or hair spray, are used to hold, improve the structure of and style the hair. The hair treatment compositions predominantly consist of a solution of film-forming resins or synthetic polymers. Hitherto mainly the following film-formers have been used in hair treatment compositions: shellac, homopolymers and copolymers of N-vinylpyrrolidone and copolymers of vinyl ethers/maleic acid half-esters, of (meth)acrylic acid or the esters and amides thereof and crotonic acid with vinyl esters. The solvent used is in the main ethanol. The polymer solution is applied to the hair by spraying. After the solvent has dried, the hair is fixed in the desired style by the polymers. The polymers should on the one hand be sufficiently hydrophilic that they can easily be washed out of the hair and, on the other hand, they should be hydrophobic, so that the hair treated with polymers holds its style even when atmospheric humidity is high, and so that individual hairs do not stick together.

However, the polymer film-formers disclosed hitherto, such as polyvinylpyrrolidones, usually have the disadvantage that the absorption of water is too high in the case of increased atmospheric humidity. As already stated, this characteristic leads to undesired sticking together of the hairs and to a loss in strength and thus the collapse of the style. If, on the other hand, the resistance to high atmospheric humidity is improved, for example in the case of copolymers of N-vinylpyrrolidone and vinyl acetate, the elasticity of the film suffers and the brittleness of these films can even lead to unpleasant dusting and a flaky coating following hair treatment. In addition, the polymers become, in particular, very much more difficult to wash out. Moreover, because of their hydrolysis-resistant C—C chains, the polymers are not biodegradable.

Shellac, on the other hand, is biodegradable, but has many disadvantages. Thus its properties as a hair treatment composition are poorer than those of the homopolymers and copolymers of N-vinylpyrrolidone, in particular in respect to the tackiness, solubility in water and rigidity. Since shellac is a natural product, its properties are also subject to substantial fluctuations.

The patents U.S. Pat. No. 4,300,580, U.S. Pat. No. 3,734,874, DE 26 33 418 B2 and WO 89/07118 disclose $NaSO_3$-containing polyesters, the main chain of which has been synthesized by a condensation reaction and of which it is to be expected that they can be degraded to shorter segments by hydrolysis of the ester groups. A disadvantage of these $NaSO_3$-containing polyesters is, however, the poor ethanol compatibility, the result of which is that the polyesters can be used only in water or water/ethanol mixtures, which, of course, dry only poorly.

Water-soluble or water-dispersible polymers, for example polyesters, polyamides or polyurethanes, are becoming increasingly important because their product properties can easily be adjusted by means of suitable starting materials. It is known that maleic anhydride and trimellitic anhydride can be used to prepare water-soluble polyesters. The anhydride group provides carboxyl groups for the solubility in water. The solubility is achieved by neutralization with the aid of amines, metal hydroxides or metal carbonates. It is known from DE-A 26 37 167 and U.S. Pat. No. 3,523,998 that polycarboxylic acids and their anhydrides make a contribution similar to that of maleic anhydride and trimellitic anhydride toward rendering polyesters soluble in water. Water-soluble polymers of this type have not been disclosed hitherto for cosmetic purposes.

The present invention relates to the use of carboxyl-containing polycondensation products having glass transition temperatures $T_G \geq 20°$ C. obtained from anhydrides of tricarboxylic or tetracarboxylic acids and diols, diamines or aminoalcohols for cosmetic purposes.

Tricarboxylic and tetracarboxylic acids which are capable of forming anhydrides are, for example:

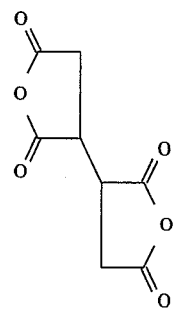

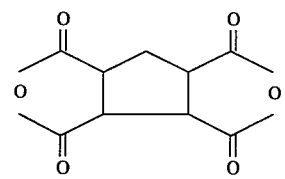

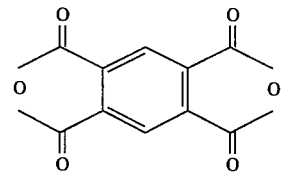

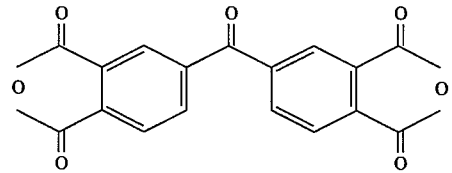

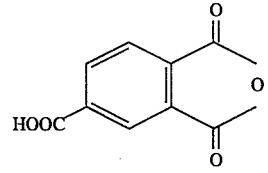

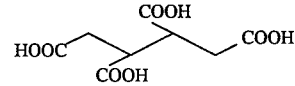

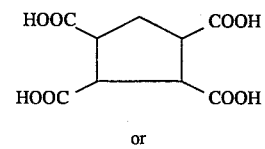

or

[Structure: tetracarboxylic benzene]

$$HOOC\text{-}C_6H_2(COOH)_3 \text{ (1,2,4,5-tetracarboxybenzene)}$$

Pyromellitic acid and in particular the monoanhydride or bisanhydride thereof, and also the compounds of the formulae

[Structure: trimellitic anhydride with free COOH]

and

[Structure: cyclopentane-tetracarboxylic dianhydride]

are preferred.

Diols, diamines and amino alcohols for the polycondensation products are, for example:

$HOCH_2CH_2OH$, $CH_3CHOHCH_2OH$, $HO(CH_2)_4OH$, $HO(CH_2)_6OH$, $HO\text{-}C_6H_{10}\text{-}OH$, $HOCH_2\text{-}C(CH_3)_2\text{-}CH_2OH$, $HOCH_2\text{-}C_6H_{10}\text{-}CH_2OH$, $HO(CH_2CH_2O)_nH$ or $HO[(CH_2)_4O]_nH$, where n is 2 to 50; compounds which have molecular weights of up to 2000 are particularly suitable. Further suitable compounds are polyesterols of phthalic, isophthalic or terephthalic acid and diols having molecular weights of up to 3000. In addition to phthalic acid, aliphatic dicarboxylic acids, such as adipic acid or succinic acid, can also be used; the phthalic acids in particular can also carry substituents, such as hydroxysulfonyl, preferably in salt form (Li, Na, K or ammonium salts).

Amine components have, for example, the formulae: $R^1HN\text{-}(CH_2)_p NHR^1$, where p is from 2 to 6 and $R^1 = C_1$- to $C_4$-alkyl,

[Structure: piperazine] $HN\diagup\diagdown NH$ or $HOCH_2CH_2NHR^1$.

A small proportion of the diols, diamines or amino alcohols can also be replaced by triols or triamines, in particular in order to achieve high molecular weights by crosslinking.

Preferred compounds of this type are, for example:

$HO(CH_2)_rOH$, $HOCH_2C(CH_3)_2CH_2OH$, $HOCH_2\text{-}CHOH\text{-}CH_3$, $HOCH_2\text{-}C_6H_{10}\text{-}CH_2OH$, $HO(C_2H_4O)_2H$,

[Structure: bis(hydroxymethyl)-dimethyl dioxanone type compound]

$HO\text{-}R^2\text{-}OOC\text{-}C_6H_3(SO_3X)\text{-}COO\text{-}R^2\text{-}OH$, where r is from 2 to 4, X is hydrogen or an alkali metal cation or ammonium cation and $R^2$ is $C_2$- to $C_8$-alkylene.

Preferred meanings of $R^2$ are, for example, $-CH_2CH_2-$, $-CH_2C(CH_3)_2CH_2-$ or $-CH_2\text{-}C_6H_{10}\text{-}CH_2-$ The polycondensation products are preferably used in the completely neutralized or partially neutralized form, for example in the form of alkali metal salts or in particular amine salts. They should have glass transition temperatures of $\geq 20°$ C. and, depending on the composition, they are water-soluble or water-dispersible and soluble or dispersible in low molecular weight alcohols or ketones.

The invention also relates to carboxyl-containing polycondensation products comprising a) structural units of the formula $$\underset{O}{\overset{R}{>}}\!\!\!CH\text{-}C(=O)\text{-}O-,$$

b) radicals derived from tricarboxylic or tetracarboxylic acids capable of anhydride formation and c) structural units derived from diols, diamines or amino alcohols, where R is hydrogen, $C_1$- to $C_8$-alkyl or phenyl, as novel compounds.

Alkyl R is, for example, $C_2H_5$, $C_3H_7$, $C_4H_9$, $C_5H_{11}$, $C_6H_{13}$, $C_7H_{15}$ or $C_8H_{17}$, n- or i- radicals being possible, and preferably methyl.

The structural units of the formula $$\underset{O}{\overset{R}{>}}\!\!\!CH\text{-}C(=O)\text{-}O-,$$

originate from an α-hydroxycarboxylic acid, such as α-hydroxyacetic acid and in particular lactic acid or derivatives thereof (for example the lactide). The products according to the invention probably also contain blocks of the formula

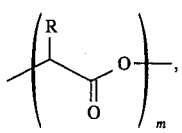

where n can be from 1 to 50, preferably from 5 to 20.

A portion of the α-hydroxycarboxylic acid (from 0 to 80%, preferably from 0 to 30%) can also be replaced by another hydroxycarboxylic acid; suitable acids are, in particular, β-hydroxycarboxylic acid, such as β-hydroxybutyric acid or β-hydroxyvaleric acid, or lactones, such as ε-caprolactone, or amino-containing hydroxycarboxylic acids, for example the reaction product of succinic anhydride and methylethanolamine of the formula

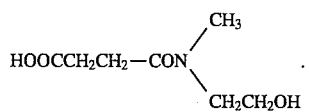

The radicals b) and c) originate from the tricarboxylic and tetracarboxylic acids and, respectively, the diols, diamines or amino alcohols already mentioned.

Depending on the composition, the compounds according to the invention are soft to brittle, water-soluble or water-dispersible, soluble or dispersible in low molecular weight alcohols or ketones and biodegradable, in particular if the proportion of structural units of the formula according to a) is >50% by weight.

If the compounds according to the invention are water-dispersible, they may be used in the form of aqueous microdispersions having particle diameters of usually from 5 to 100 nm, in particular from 10 to 80 nm and solids contents of usually from 1 to 40% by weight, in particular from 3 to 30% by weight. These microdispersions generally require no emulsifiers or surfactants for their stabilization.

The invention relates in particular to polycondensation products which contain
from 30 to 87% by weight of a),
from 10 to 32% by weight of b) and
from 3 to 48% by weight of c)
and are suitable as hair treatment compositions.

Products which contain
from 40 to 80% by weight of a),
from 16 to 30% by weight of b) and
from 4 to 30% by weight of c)
are preferred for this purpose.

The procedure for the preparation of the polycondensation products according to the invention is expediently to mix the starting compounds for a), b) and c) and to heat the mixture under an inert gas atmosphere to from about 110° to 240° C. preferably from 130° to 200° C., and to distill off the water thus formed. The addition of conventional esterification catalysts such as tetraisopropyl titanate (in the customary amounts, for example from 10 to 50 ppm) is expedient.

The reaction can also be started in the presence of inert organic solvents, which are distilled off again in the course of the reaction. Such solvents are, for example, water, tetrahydrofuran or ethylene glycol dimethyl ether. Solvent is distilled off until the reaction mixture remains permanently clear. After the reaction, that is to say when the acid number of the product has reached the desired value, the reaction mixture is heated for from about 3 to about 5 h at from 150° to 200° C. under reduced pressure.

Details of the reaction procedure can be taken from the examples, in which, unless indicated otherwise, parts and percentages are by weight.

The products according to the invention as a rule have K values of from 10 to 90, preferably 20 to 50, determined by the Fikentscher method (1% strength NMP solution, 25° C., pH 7) and acid numbers of from 10 to 200, preferably 40 to 150.

For use as hair treatment compositions, the carboxyl groups in the products according to the invention should preferably be in salt form, sodium and ammonium ions derived from the compounds 2-amino-2-methylpropanol, diethylaminopropylamine, triisopropanolamine, methyldiethanolamine, dimethylethanolamine and imidazole being preferred.

EXAMPLES

General method for the preparation of water-soluble polyesters:

In a four-necked flask provided with a stirrer, an internal thermometer, a gas inlet tube and a descending condenser, lactic acid (90% strength solution) diol (or diamine or amino alcohol) and anhydride are heated together, under nitrogen and with stirring, to 150° C., the water first being distilled off from the lactic acid solution at about 100° C. The reaction temperature is kept at 150° for about 3 h and is then raised by 10° C. per hour until it reaches about 200°±20° C. The water of reaction is distilled off until approximately the theoretical acid number is obtained. The reaction mixture is then heated, also with the addition of catalyst if necessary, for a further 2–4 hours under a reduced pressure of about 10 mmHg. After cooling to room temperature, a clear, pale yellow to yellow product is obtained which after neutralization with 2-amino-2-methylpropanol is readily soluble or dispersible in water and in ethanol.

The following abbreviations are used in the examples (the products were prepared by the general method).
LA=90% strength aqueous solution of lactic acid
EG=ethylene glycol
TMP=trimethylolpropane
PMDA=pyromellitic acid dianhydride
P(IPA:NPG)=polyester-diol $M_W$=800 g/mol was prepared from isophthalic acid and neopentyl glycol.
P(SIPA:NPG)=has the structure

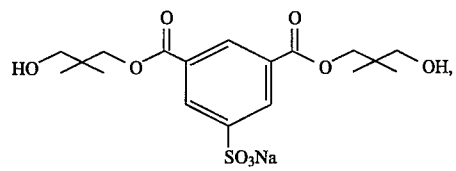

and was prepared from 5-(sodiumsulfonato)-isophthalic acid and neopentyl glycol.

| Ex. No. | Com-position [mol %] | Acid number | $T_G$[1] [°C.] | K value 1% strength in NMP | Solubility[2] in EtOH | Solubility[2] $H_2O$ | Curl Retention (25° C., 90% relative humidity, 5 h) | Biodegradability BOD30/COD | Zahn-Wellens [%] |
|---|---|---|---|---|---|---|---|---|---|
| 1 | LA [10] EG [1] PMDA [1] | 128 | 57 | 25.7 | sol. | sol. | 49.0 | 31.8% | 91 |
| 2 | LA [10] EG [0.85] TMP [0.1] PMDA [1] | 118 | 62 | 37.0 | sol. | disp. | 51.3 | 32.0% | 94 |
| 3 | LA [10] P(IPA-NPG) [1] PMDA [1] | 101 | 54 | 19.6 | sol. | disp. | 59.0 | 36.0% | — |
| 4 | LA [10] N-methyl-ethanol-amine [1] PMDA [1] | 116 | 61 | 21.7 | sol. | sol. | 32.0 | 27.0% | — |
| 5 | la [10] P(SIPA-NPG) [1] NPG [2] PMDA [3] | 117 | 53 | 35.4 | insol. | disp. | 46.0[3] | 19.0% | 96 |
| 6 | — P(IPA:NPG) [1] PMDA [1] | 112 | 59 | 22.9 | sol. | sol. | 56.0 | −6.0% | — |

[1] Glass transition temperature = $T_G$ was determined by differential thermal analysis method ASTM D 3418.
[2] The solubility was determined following neutralization with 2-amino-2-methylpropanol to pH 7 (5% strength solution, RT).
[3] The curl retention of product 5 was determined in ethanol/water (4:1) because the product was insoluble in ethanol.

Further test methods used:
1. Curl retention:

The curl retention is a measure of the hair holding effect. It is measured in a model experiment on hair curls produced by a conventional water-wave on approximately 15 cm long hair which has been sprayed for 4 seconds from a distance of 10 cm with 2% strength spray solution of a resin according to Table 1 or 2 and 75% neutralized. After treating the suspended curls for 5 hours in a climatic chamber (25° C., 90% relative atmospheric humidity), the relative deformation (widening) of the curls with respect to the original shape is determined. A high value indicates a high holding effect, i.e. 100% would be retention of the original shape of the suspended curls; 0% would be completely straightened hair.

2. Biodegradability
2.1. BOD30/COD
BOD: Methods for determination of the biochemical oxygen demand according to analytical method: DIN 38409 part 51
BOD 30: BOD after 30 days.
COD: Method for determining the chemical oxygen demand according to analytical method: DIN 38409, part 41.
2.2 Zahn-Wellens creep test: after 28 days
Analytical method: DIN 38412, part 25.

Use Examples
1. Aerosol hair spray

| | |
|---|---|
| Polymer according to Example 2 | 3.00% |
| 2-Amino-2-methylpropanol | 0.64% |
| Ethanol | 51.36% |
| Distilled water | 10.00% |
| Dimethyl ether | 35.00% |
| Perfume oil | q.s. |

2. Hand pump hair spray

| | |
|---|---|
| Polymer according to Example 2 | 3.00% |
| 2-Amino-2-methylpropanol | 0.64% |
| Ethanol | 20.45% |
| Distilled water | 40.91% |
| Perfume oil | q.s. |

3. Styling lotion

| | |
|---|---|
| Polymer according to Example 1 | 4.00% |
| 2-Amino-2-methylpropanol | 0.82% |
| Distilled water | 95.18% |
| Perfume oil | q.s. |

4. Styling lotion

| | |
|---|---|
| Polymer according to Example 1 | 4.00% |
| 2-Amino-2-methylpropanol | 0.82% |
| Ethanol | 31.73% |
| Distilled water | 63.45% |
| Perfume oil | q.s. |

We claim:

1. A carboxyl-containing polycondensation product comprising a) structural units of the formula

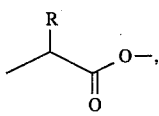

b) radicals derived from tricarboxylic or tetracarboxylic acids capable of anhydride formation and c) structural units derived from diols, diamines or amino alcohols, where R is hydrogen, $C_1$- to $C_8$-alkyl or phenyl.

2. A polycondensation product as claimed in claim 1, containing as component b) pyromellitic acid, the monoanhydride or dianhydride thereof or the compounds of the formulae

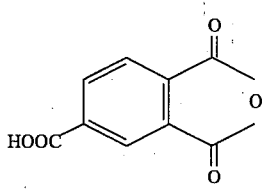

and

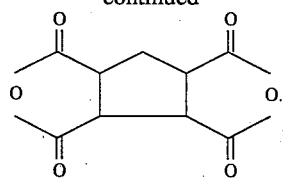

3. A polycondensation product as claimed in claim 1, which contains from 30 to 87% by weight of a), from 10 to 32% by weight of b) and from 3 to 48% by weight of c).

4. A product as claimed in claim 1 containing from 40 to 80% by weight of a), from 16 to 30% by weight of b) and from 4 to 30% by weight of c).

5. A hair treatment composition containing a polycondensation product as claimed in claim 2 and a cosmetically acceptable carrier.

6. A hair treatment composition as claimed in claim 5, wherein the carrier is an alcohol, ketone or water.

7. A hair treatment composition containing a polycondensation produced as claimed in claim 1 and a carrier.

8. A hair treatment composition containing a polycondensation product as claimed in claim 1, in the form of an aqueous microdispersion.

* * * * *

UNITED STATES PATENT AND TRADEMARK OFFICE
CERTIFICATE OF CORRECTION

PATENT NO.   :   5,498,690
DATED        :   March 12, 1996
INVENTOR(S)  :   Son N. KIM et al.

It is certified that error appears in the above-indentified patent and that said Letters Patent is hereby corrected as shown below:

On the title page, Item [86], the PCT number is incorrect. It should read:

--[86]  PCT No.:  PCT/EP93/01887--

Signed and Sealed this

Fourth Day of June, 1996

Attest:

BRUCE LEHMAN

Attesting Officer          Commissioner of Patents and Trademarks